United States Patent
Iwane et al.

(10) Patent No.: US 12,336,693 B2
(45) Date of Patent: Jun. 24, 2025

(54) MEDICAL SYSTEM, MEDICAL LIGHT SOURCE APPARATUS, AND METHOD IN MEDICAL LIGHT SOURCE APPARATUS

(71) Applicant: Sony Corporation, Tokyo (JP)

(72) Inventors: Tetsuaki Iwane, Tokyo (JP); Tomoyuki Oki, Tokyo (JP)

(73) Assignee: Sony Corporation, Tokyo (JP)

( * ) Notice: Subject to any disclaimer, the term of this patent is extended or adjusted under 35 U.S.C. 154(b) by 415 days.

(21) Appl. No.: 17/258,745

(22) PCT Filed: Aug. 7, 2019

(86) PCT No.: PCT/JP2019/031277
§ 371 (c)(1),
(2) Date: Jan. 8, 2021

(87) PCT Pub. No.: WO2020/036112
PCT Pub. Date: Feb. 20, 2020

(65) Prior Publication Data
US 2021/0267446 A1  Sep. 2, 2021

(30) Foreign Application Priority Data
Aug. 13, 2018  (JP) ................................ 2018-152375

(51) Int. Cl.
*A61B 1/07* (2006.01)
*A61B 1/00* (2006.01)
(Continued)

(52) U.S. Cl.
CPC ............ *A61B 1/07* (2013.01); *A61B 1/00096* (2013.01); *A61B 1/05* (2013.01); *A61B 1/0638* (2013.01)

(58) Field of Classification Search
CPC ......... A61B 1/07; A61B 1/00096; A61B 1/05; A61B 1/0638; A61B 1/043; A61B 1/042;
(Continued)

(56) References Cited

U.S. PATENT DOCUMENTS 10,058,231 B2 * 8/2018 Nakatate ............ A61B 1/00096
11,953,376 B2 * 4/2024 Takashima ........... H04N 25/135
(Continued)

FOREIGN PATENT DOCUMENTS

CN        1163000 A      10/1997
CN      101821872 A       9/2010
(Continued)

OTHER PUBLICATIONS

International Search Report and Written Opinion mailed on Oct. 1, 2019, received for PCT Application PCT/JP2019/031277, Filed on Aug. 7, 2019, 9 pages including English Translation.

*Primary Examiner* — John P Leubecker
*Assistant Examiner* — Li-Ting Song
(74) *Attorney, Agent, or Firm* — XSENSUS LLP

(57) ABSTRACT

To generate light with high color rendering properties while suppressing an occurrence of unevenness. The present disclosure provides a medical system (3000, 6000) including: a medical device (2000, 4000) provided with an imaging unit configured to image an observation object; and a light source apparatus (1000) configured to generate light to irradiate the observation object, wherein the light source apparatus has: a narrow-band light source (100) configured to emit narrow-band light of which a wavelength width is a narrow band; a wide-band light source (200) configured to emit wide-band light of which the wavelength width is wider than the narrow-band light; a combining unit (310) configured to combine the narrow-band light and the wide-band (Continued)

light; and an emission angle converting unit (400) configured to convert an emission angle of the narrow-band light.

16 Claims, 14 Drawing Sheets

(51) Int. Cl.
  *A61B 1/05* (2006.01)
  *A61B 1/06* (2006.01)
(58) Field of Classification Search
  CPC .............. A61B 1/00163; A61B 1/0661; G02B 23/2461; G02B 23/2469; B02B 27/1006
  USPC .................................................. 600/178, 180
  See application file for complete search history.

(56) References Cited

U.S. PATENT DOCUMENTS

| | | | | |
|---|---|---|---|---|
| 2002/0171831 | A1* | 11/2002 | Backman | A61B 5/0084 |
| | | | | 356/369 |
| 2008/0225410 | A1* | 9/2008 | Ning | G02B 7/007 |
| | | | | 359/830 |
| 2012/0083656 | A1* | 4/2012 | Kuroda | A61B 1/063 |
| | | | | 600/165 |
| 2012/0206922 | A1 | 8/2012 | Feklistov | |
| 2013/0155648 | A1* | 6/2013 | Morgenbrod | G02B 27/0944 |
| | | | | 600/249 |
| 2014/0005483 | A1* | 1/2014 | Ohashi | A61B 1/0646 |
| | | | | 600/162 |
| 2014/0012113 | A1* | 1/2014 | Kaku | A61B 1/0638 |
| | | | | 600/339 |
| 2015/0109759 | A1* | 4/2015 | Sugano | A61B 1/128 |
| | | | | 362/84 |
| 2017/0095144 | A1 | 4/2017 | Tabata et al. | |
| 2017/0100024 | A1* | 4/2017 | Shahmoon | G02B 6/02042 |
| 2017/0245746 | A1* | 8/2017 | Komazaki | G02B 23/2469 |
| 2018/0183981 | A1* | 6/2018 | Talbert | H04N 23/56 |
| 2020/0397269 | A1* | 12/2020 | Miyata | G02B 27/48 |
| 2021/0251478 | A1* | 8/2021 | Mao | A61B 1/04 |
| 2024/0280490 | A1* | 8/2024 | Perry | G02B 21/0032 |

FOREIGN PATENT DOCUMENTS

| | | | |
|---|---|---|---|
| CN | 107209395 A | 9/2017 | |
| EP | 3574819 A1 | 12/2019 | |
| JP | 2006-6803 A | 1/2006 | |
| JP | 2012-75562 A | 4/2012 | |
| JP | 2015-223462 A | 12/2015 | |
| JP | 2016-120104 A | 7/2016 | |
| JP | 2016120105 A | 7/2016 | |
| JP | 2016137309 A | 8/2016 | |
| JP | 2017-187543 A | 10/2017 | |
| KR | 20180070250 A | 6/2018 | |
| WO | 2015/194312 A1 | 12/2015 | |
| WO | WO-2016103643 A1 * | 6/2016 | ............ A61B 1/042 |
| WO | WO-2018125936 A1 | 7/2018 | |
| WO | WO-2018139101 A1 | 8/2018 | |
| WO | WO-2019198293 A1 * | 10/2019 | |
| WO | WO-2020080223 A1 * | 4/2020 | |

* cited by examiner

MEDICAL SYSTEM, MEDICAL LIGHT SOURCE APPARATUS, AND METHOD IN MEDICAL LIGHT SOURCE APPARATUS

CROSS-REFERENCE TO RELATED APPLICATIONS

The present application is based on PCT filing PCT/JP2019/031277, filed Aug. 7, 2019, which claims priority to JP 2018-152375, filed Aug. 13, 2018, the entire contents of each are incorporated herein by its reference.

TECHNICAL FIELD

The present disclosure relates to a medical system, a medical light source apparatus, and a method in the medical light source apparatus.

BACKGROUND ART

Conventionally for example, PTL 1 below describes providing at least one laser light source and causing light from the laser light source to enter a light guide.

CITATION LIST

Patent Literature

[PTL 1]
JP 2015-223462 A

SUMMARY

Technical Problem

Light sources for medical use such as that described in the patent literature mentioned above mainly use a lamp light source (a xenon lamp or a halogen lamp) or a white LED. However, since these light sources have a large light emission point and a wide emission angle, it is difficult to collect light on a small-diameter light guide in an efficient manner.

Therefore, conceivably using a semiconductor laser with a small light emission point and a narrow emission angle, white light may be generated by combining red light, green light, and blue light to be used as a medical light source. However, since a semiconductor laser has a narrow wavelength width, for example, white light generated by combining red light, green light, and blue light has reduced color rendering properties. When white light generated by a semiconductor laser is combined with white light obtained from another light source in order to increase the color rendering properties of the white light generated by the semiconductor laser, a problem occurs in that a difference in emission angles of the two beams of white light causes a deviation in hues of white light and ends up creating unevenness. This is attributable to the fact that an emission angle distribution of the white light generated by a semiconductor laser has a Gaussian shape but an emission angle distribution of the white light from other light sources (such as an LED) has a Lambertian shape.

In particular, when medical applications are assumed, a decline in color rendering properties and an occurrence of unevenness may possibly cause an operator (a medical doctor) to make an erroneous diagnosis when determining a lesion, a tumor, or the like of an affected area based on color. In addition, in a case of an image where color rendering properties and unevenness are ensured only in a central portion of the image, since a device such as an endoscope or a microscope must be operated so that an affected area is moved to the center of the image in order to enable an operator to make correct decisions, an extremely complicated operation must be performed.

In consideration thereof, there are demands for generating light with high color rendering properties while suppressing an occurrence of unevenness.

Solution to Problem

The present disclosure provides a medical system including: a medical device provided with an imaging unit configured to image an observation object; and a light source apparatus configured to generate light to irradiate the observation object, wherein the light source apparatus has: a narrow-band light source configured to emit narrow-band light of which a wavelength width is a narrow band; a wide-band light source configured to emit wide-band light of which the wavelength width is wider than the narrow-band light; a combining unit configured to combine the narrow-band light and the wide-band light; and an emission angle converting unit configured to convert an emission angle of the narrow-band light.

In addition, the present disclosure provides a medical light source apparatus including: a narrow-band light source configured to emit narrow-band light of which a wavelength width is a narrow band; a wide-band light source configured to emit wide-band light of which the wavelength width is wider than the narrow-band light; a combining unit configured to combine the narrow-band light and the wide-band light; and an emission angle converting unit configured to convert an emission angle of the narrow-band light.

Furthermore, the present disclosure provides a method in a medical light source apparatus including the steps of: combining narrow-band light of which a wavelength width is a narrow band and wide-band light of which the wavelength width is wider than the narrow-band light; and converting an emission angle of the narrow-band light prior to combining the narrow-band light and the wide-band light.

Advantageous Effects of Invention

According to the present disclosure, light with high color rendering properties can be generated while suppressing an occurrence of unevenness.

It should be noted that the advantageous effect described above is not necessarily restrictive and, in addition to the advantageous effect described above or in place of the advantageous effect described above, any of the advantageous effects described in the present specification or other advantageous effects that can be comprehended from the present specification may be produced.

DESCRIPTION OF EMBODIMENTS

Figure 1:
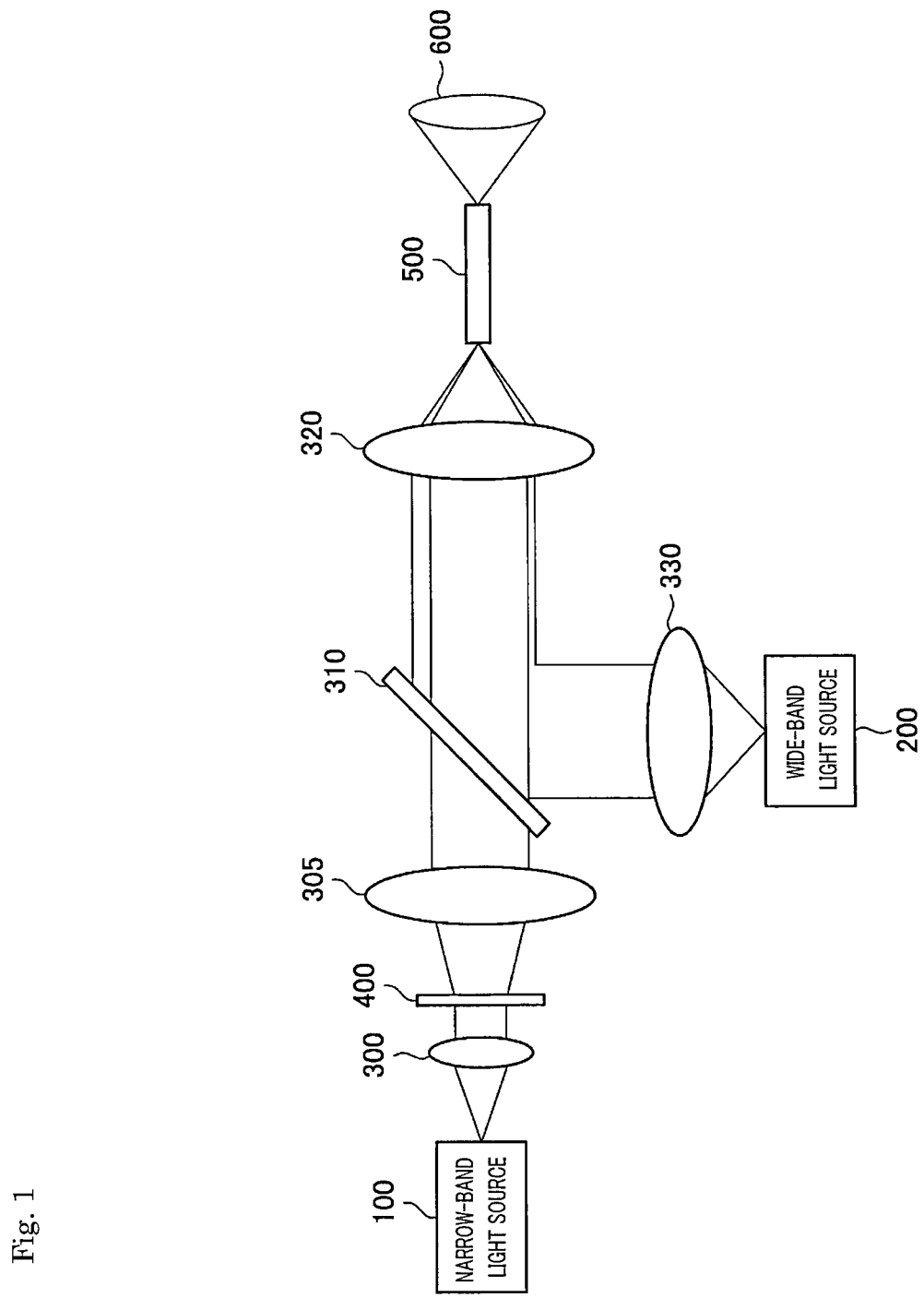
FIG. 1 is a schematic diagram showing a schematic configuration of a light source apparatus and a periphery thereof according to an embodiment of the present disclosure.

Hereinafter, a preferred embodiment of the present disclosure will be described in detail with reference to the accompanying drawings. In the present specification and the drawings, components having substantially a same functional configuration will be denoted by same reference signs and overlapping descriptions thereof will be omitted.

Descriptions will be given in the following order.
1. Background
2. Configuration of light source apparatus
3. Conversion of emission angle by emission angle converting element
4. NA limitation of wide-band light
5. Example of emission angle converting element
6. Example of NA limitation of wide-band light
7. Configuration example of narrow-band light source
8. Configuration example of narrow-band light source including yellow light source
9. Configuration example of medical system
9.1. Configuration example of endoscopic system
9.2. Configuration example of microscopic system

1. BACKGROUND

Endoscopes are being widely used as apparatuses for observing an internal structure of an object. In particular, in the field of medicine, there has been a rapid proliferation of endoscopes in accordance with advances in operative procedures and techniques, making endoscopes essential in many of today's diagnostic fields. In recent years, endoscopic apparatuses have been required to be minimally invasive with respect to a patient regardless of whether the endoscopic apparatuses are flexible scopes or rigid scopes and, in particular, improvements have been made towards making a scope portion that comes into direct contact with a patient narrower and smaller. Accordingly a challenge for light source apparatuses as lighting apparatuses that illuminate an affected area is to efficiently guide light to ever narrower light guides. While a lamp light source (a xenon lamp or a halogen lamp) or a white LED is mainly used as a light source for providing illumination in a conventional endoscopic apparatus, since both light sources have a large light emission point and a wide emission angle (a large etendue), it is difficult to collect light on a small-diameter light guide in an efficient manner.

In consideration thereof, the present embodiment proposes a light source apparatus using a semiconductor laser (LD) with a small light emission point and a narrow emission angle (a small etendue). On the other hand, it is generally known that, since a semiconductor laser has a narrow wavelength width, for example, white light generated by combining red light, green light, and blue light has inferior color rendering properties. Deterioration of color rendering properties may possibly cause a medical doctor to make an erroneous diagnosis during an endoscopic observation when, for example, determining a malignant tumor or the like. In consideration thereof, in the present embodiment, a light source with a wide wavelength width is mixed with laser light as an auxiliary light source to improve color rendering properties. In particular, since white light generated by combining red light, green light, and blue light lacks light with intermediate wavelengths of these colors, mixing the white light with a light source with a wide wavelength width enables a hue of white light to be optimized and color rendering properties to be improved.

Generally a light guide (LG) that is a bundle of optical fibers for guiding light from a light source emits illuminating light that retains an emission angle distribution of incident light. Therefore, when guiding light from a semiconductor laser to a light guide, since laser light generally has an emission angle distribution with a Gaussian shape, illuminating light is produced which is bright around an optical axis but becomes darker toward its periphery.

On the other hand, since wide-band light (for example, a white LED) to be used as an auxiliary light source generally has an emission angle distribution with a Lambertian shape, illuminating light is produced of which light intensity does not decrease even in its periphery. When combining the two types of light with different emission angle distributions, since a deviation in proportions of the laser light and the wide-band light arises between a central portion and a periphery, unevenness (in particular, color unevenness) occurs in illuminating light. For this reason, when mixing an auxiliary light source such as a white LED with laser light, a deviation occurs in the hue of white light. Therefore, in order to mix an auxiliary light source such as a white LED with laser light to realize a light source with high color rendering properties, such unevenness in illuminating light must be suppressed. For example, when unevenness is greater in the periphery than at the center, there is a possibility that a medical doctor may make an erroneous diagnosis when observing the periphery. In consideration thereof, the present embodiment proposes a light source apparatus for suppressing unevenness in illuminating light. Hereinafter, a detailed description will be given.

2. CONFIGURATION OF LIGHT SOURCE APPARATUS

First, with reference to FIG. 1, a schematic configuration of a light source apparatus 1000 and a periphery thereof according to an embodiment of the present disclosure will be described. As shown in FIG. 1, the light source apparatus 1000 according to the present embodiment is constituted by a narrow-band light source 100, a wide-band light source 200, a lens 300, a lens 305, a dichroic mirror (a combining unit) 310, a lens 320, a lens 330, and an emission angle converting element (an emission angle converting unit) 400. Light emitted from the light source apparatus 1000 passes through a light guide 500 and is guided to an observation optical system 600.

The narrow-band light source 100 is constituted by a semiconductor laser and emits narrow-band light. The wide-band light source 200 is constituted by a white LED and emits white wide-band light. While a white LED is exemplified as the wide-band light source 200, the wide-band light source 200 may be a light source such as a xenon lamp or a halogen lamp. Alternatively the wide-band light source 200 may be a fluorescent body that emits fluorescence.

The narrow-band light is collimated by the lens 300 and enters the emission angle converting element 400. The emission angle converting element 400 is assumed to be, for example, a diffuser plate and has a role of imparting a desired light distribution angle to incident collimated light and converting an emission angle distribution. Light emitted from the emission angle converting element 400 is collimated by the lens 305, passes through the combining dichroic mirror 310, and is collected on the light guide 500 by the lens 320.

On the other hand, the wide-band light is collimated by the lens 330, reflected by the dichroic mirror 310 and combined with the narrow-band light, and is collected on the light guide 500 by the lens 320.

The dichroic mirror 310 has a characteristic of transmitting a wavelength component of the narrow-band light and reflecting other wavelength bands. The narrow-band light and the wide-band light can be combined by the dichroic mirror 310. As a combining method, methods such as wavelength combining, polarization combining, and spatial combining can be used.

As the light guide 500, a bundle of multimode fibers of several ten μm that are frequently used in medical apparatuses can be used. Collected illuminating light is guided to the observation optical system 600 through the light guide 500. The observation optical system 600 corresponds to an intrascope optical system in the case of an endoscope application and to a microscope optical system in the case of a microscope application, and light emitted from the light source apparatus 1000 irradiates an actual observation object as illuminating light through these optical systems.

3. CONVERSION OF EMISSION ANGLE BY EMISSION ANGLE CONVERTING ELEMENT

Figure 2:
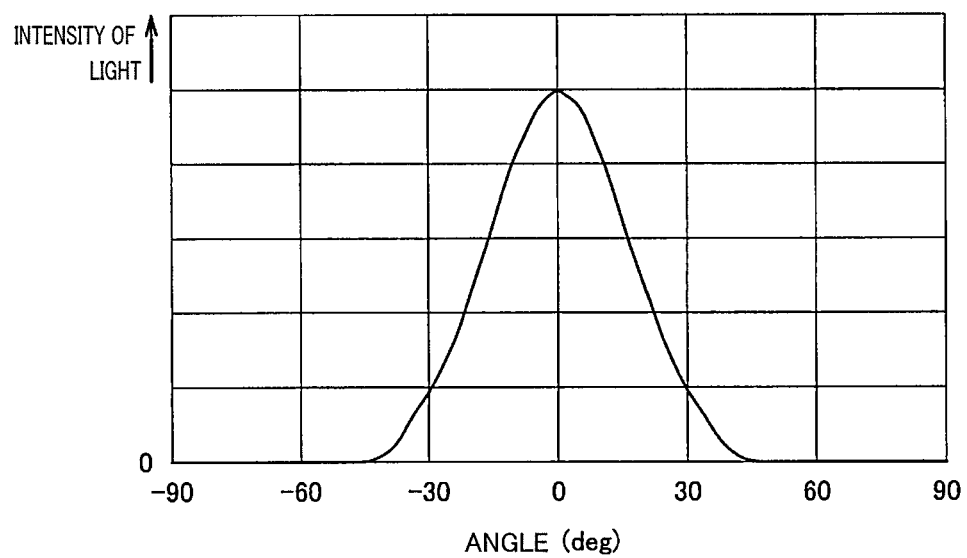
FIG. 2 is a characteristic diagram showing an emission angle distribution of narrow-band light.

FIG. 2 is a characteristic diagram showing an emission angle distribution of the narrow-band light. In FIG. 2, an abscissa represents an emission angle and an ordinate represents intensity of light. The narrow-band light has high intensity of light in the vicinity of a 0-degree emission angle, and a distribution of intensity with respect to the emission angle is a Gaussian distribution.

Figure 3:
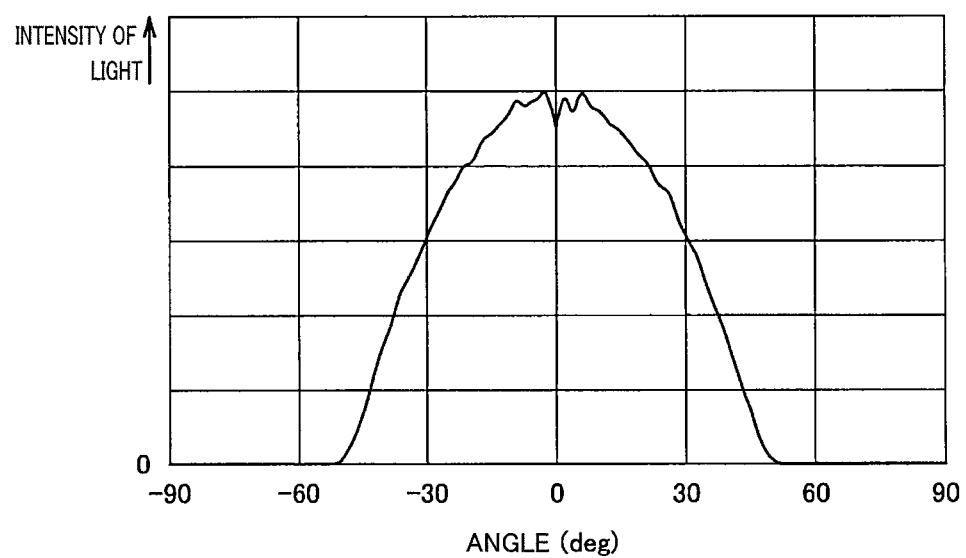
FIG. 3 is a characteristic diagram showing an emission angle distribution of wide-band light.

FIG. 3 is a characteristic diagram showing an emission angle distribution of the wide-band light. In FIG. 3, similarly an abscissa represents an emission angle and an ordinate represents intensity of light. Compared to the narrow-band light, the wide-band light has less variation of intensity of light in the vicinity of a 0-degree emission angle, and a distribution of intensity of light with respect to the emission angle is a Lambertian distribution.

Figure 4:
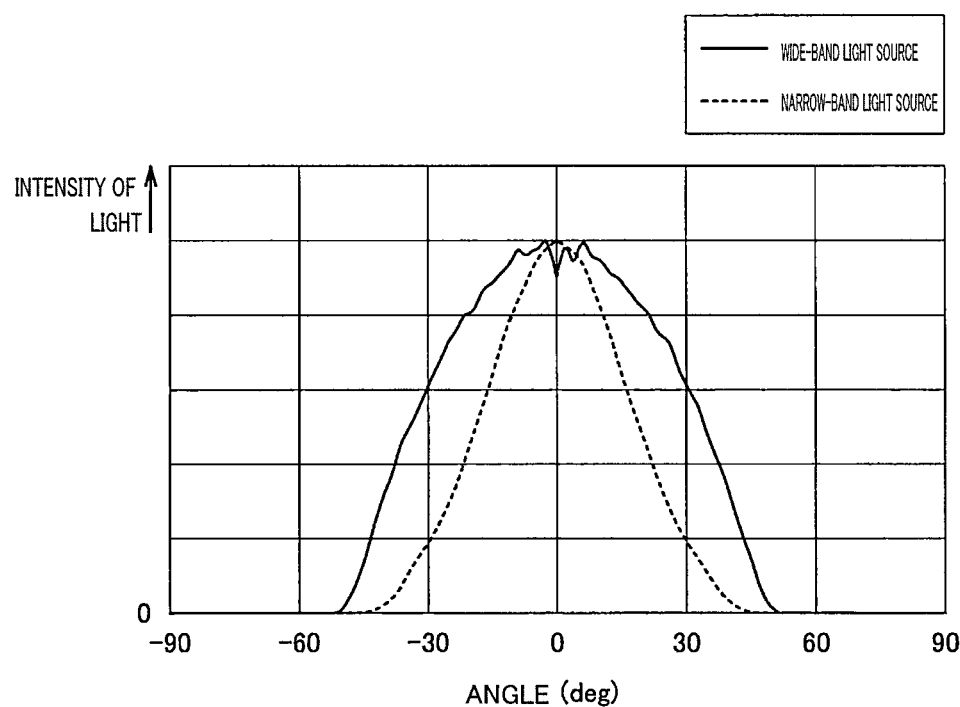
FIG. 4 is a characteristic diagram showing the emission angle distribution of narrow-band light shown in FIG. 2 and the emission angle distribution of wide-band light shown in FIG. 3 being overlaid on each other.

FIG. 4 is a characteristic diagram showing the emission angle distribution of the narrow-band light shown in FIG. 2 and the emission angle distribution of the wide-band light shown in FIG. 3 being overlaid on each other and represents a state where the narrow-band light and the wide-band light have been combined as-is. As shown in FIG. 4, while intensities of the wide-band light source and the narrow-band light source are more or less the same near a central portion (0-degree emission angle), the closer to the periphery the greater an amount of decrease of intensity of the narrow-band light source. This indicates that an intensity ratio between the narrow-band light source and the wide-band light source differs between the central portion and the periphery and that the unevenness described earlier occurs.

Figure 5:
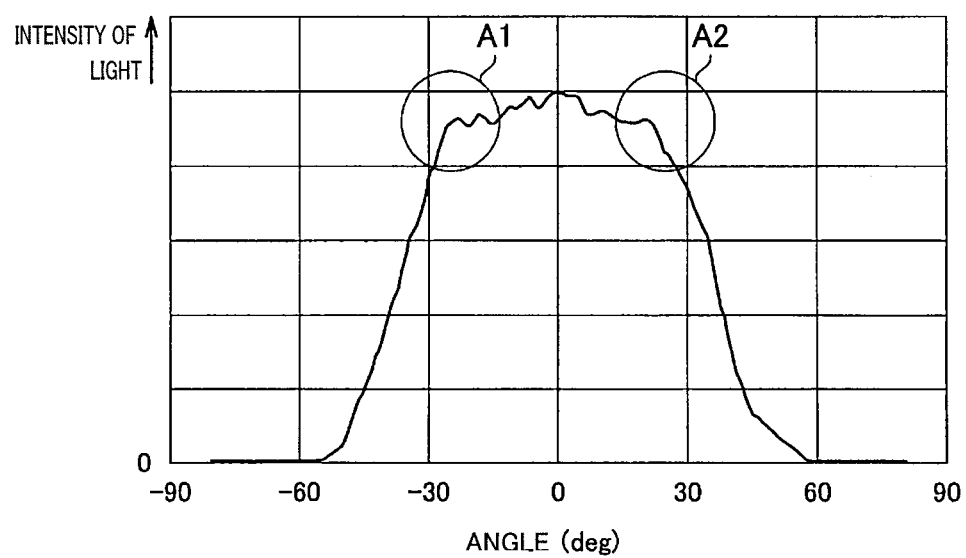
FIG. 5 is a characteristic diagram showing an emission angle distribution of narrow-band light after being transmitted through an emission angle converting element.

Therefore, in the present embodiment, by having the emission angle converting element 400 transmit the narrow-band light to control the emission angle distribution of the narrow-band light, the emission angle distribution of the narrow-band light is brought close to the emission angle distribution of the wide-band light. FIG. 5 is a characteristic diagram showing the emission angle distribution of the narrow-band light after being transmitted through the emission angle converting element 400. As shown in FIG. 5, by passing through the emission angle converting element 400, the emission angle distribution of the narrow-band light widens and the emission angle distribution of the narrow-band light acquires characteristics similar to those of the emission angle distribution of the wide-band light. In particular, by causing light collimated by the lens 300 to enter the emission angle converting element 400, the emission angle distribution can be converted into a desired state and an effect of changing the emission angle distribution can be enhanced.

Therefore, since combining the narrow-band light having passed through the emission angle converting element 400 and the wide-band light causes amounts of decrease of intensity of the narrow-band light and the wide-band light to match each other from the central portion toward the periphery intensity ratios between the narrow-band light source and the wide-band light source between the central portion and the periphery match each other. Accordingly an occurrence of unevenness can be reliably suppressed.

4. NA LIMITATION OF WIDE-BAND LIGHT

Figure 6:
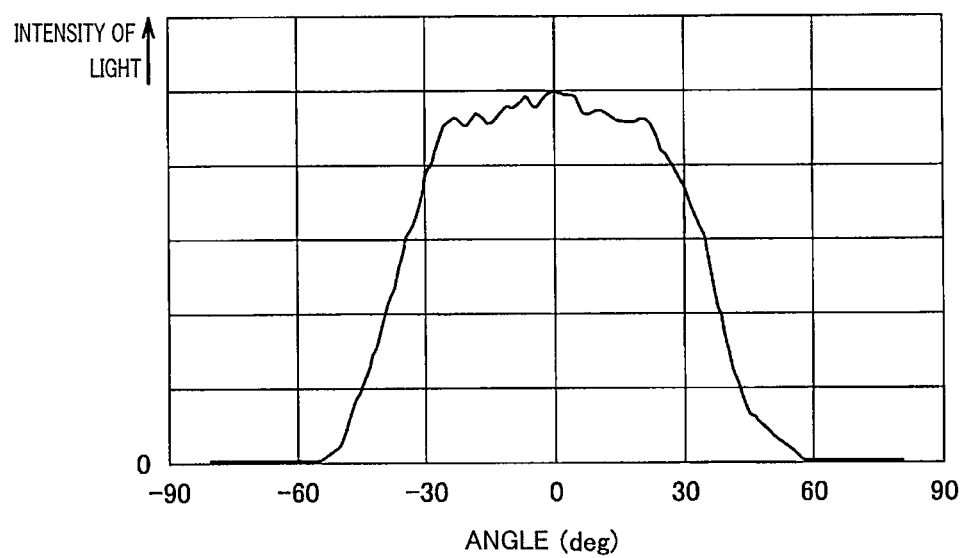
FIG. 6 is a characteristic diagram showing characteristics of wide-band light of which an emission angle distribution has been changed by applying NA limitation to the wide-band light shown in FIG. 3.

In the present embodiment, a limitation of an NA (Numerical Aperture) is performed with respect to the wide-band light. NA limitation is performed by making an NA of the lens 330 shown in FIG. 1 smaller than an emission angle of the wide-band light source. The NA is a numerical value that is a sine expression of a size of a maximum light-receiving angle (a numerical aperture). FIG. 6 is a characteristic diagram showing characteristics of the wide-band light of which an emission angle distribution has been changed by applying NA limitation to the wide-band light shown in FIG. 3.

Figure 7:
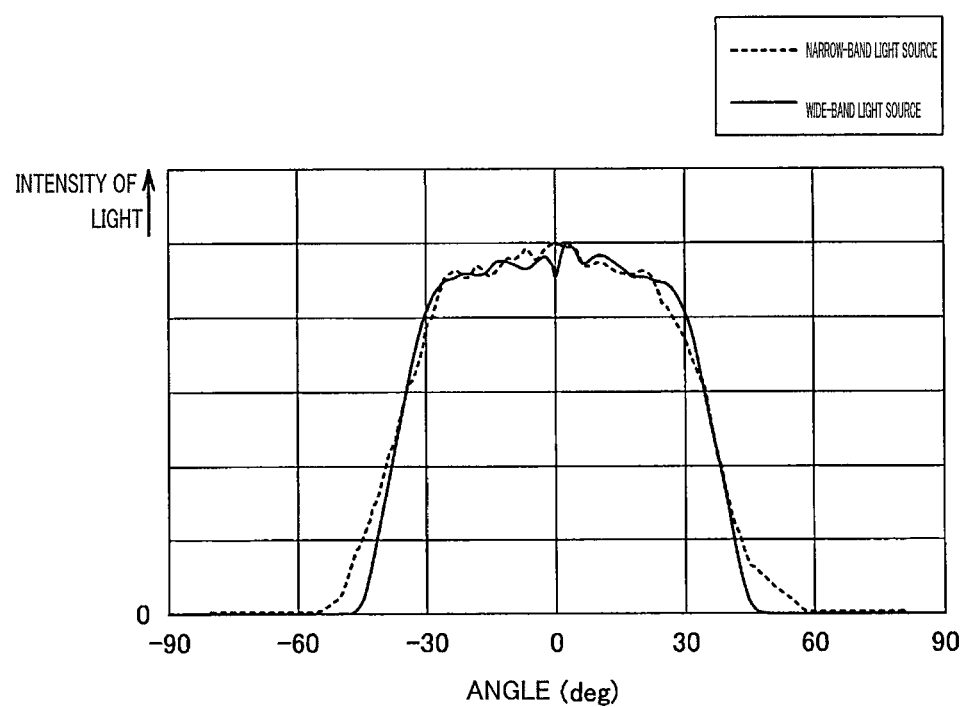
FIG. 7 is a characteristic diagram showing the emission angle distribution of narrow-band light after being transmitted through an emission angle converting element shown in FIG. 5 and the emission angle distribution of wide-band light having been subjected to NA limitation shown in FIG. 6 being overlaid on each other.

FIG. 7 is a characteristic diagram showing the emission angle distribution of the narrow-band light having passed through the emission angle converting element 400 shown in FIG. 5 and the emission angle distribution of the wide-band light having been subjected to NA limitation shown in FIG.

6 being overlaid on each other and represents a state where the narrow-band light having passed through the emission angle converting element 400 and the wide-band light having been subjected to NA limitation are combined.

In this manner, by intentionally reducing the NA of the lens 330, a component with a wide emission angle of the wide-band light can be removed and the emission angle distribution of the narrow-band light and the emission angle distribution of the wide-band light can be made characteristics that more close approximate each other. Accordingly an occurrence of unevenness can be more reliably suppressed.

5. EXAMPLE OF EMISSION ANGLE CONVERTING ELEMENT

As described above, the emission angle converting element 400 has a function of converting the emission angle distribution of the narrow-band light and widening the emission angle of the narrow-band light. A diffuser plate can be used as the emission angle converting element 400. Using a diffuser plate has advantages such as enabling an optical system to be constructed in a small size, enabling manufacturing cost to be reduced, and the like.

As the diffuser plate, a top-hat diffuser plate is particularly preferably used. Using a top-hat diffuser plate enables hat-shaped characteristics of which edges are formed by a region A1 and a region A2 as shown in FIG. 5 to be obtained. Accordingly a decline in peripheral light intensity of the narrow-band light can be suppressed and the emission angle distributions of the narrow-band light and the wide-band light can be made to approximate each other.

Alternatively a fly-eye lens can also be used as the emission angle converting element 400. A fly-eye lens has redundancy and a wide margin in terms of an angle of incident light and, even when a degree of collimation of the narrow-band light by the lens 300 is reduced, an effect on characteristics after emission angle conversion is small. In addition, when using a fly-eye lens, edges of the regions A1 and A2 shown in FIG. 5 can be made sharper. Therefore, when desiring to secure a wider image region such as when considering the edges of the regions A1 and A2 to be borders of an image region, a fly-eye lens is preferably used.

On the other hand, since two fly-eye lenses are usually used as a pair, a top-hat diffuser plate has higher transmittance of light. Therefore, when desiring to secure higher light intensity or the like, a top-hat diffuser plate is preferably used. In addition, using a top-hat diffuser plate is also advantageous in terms of reducing cost and conserving space.

Figure 8:
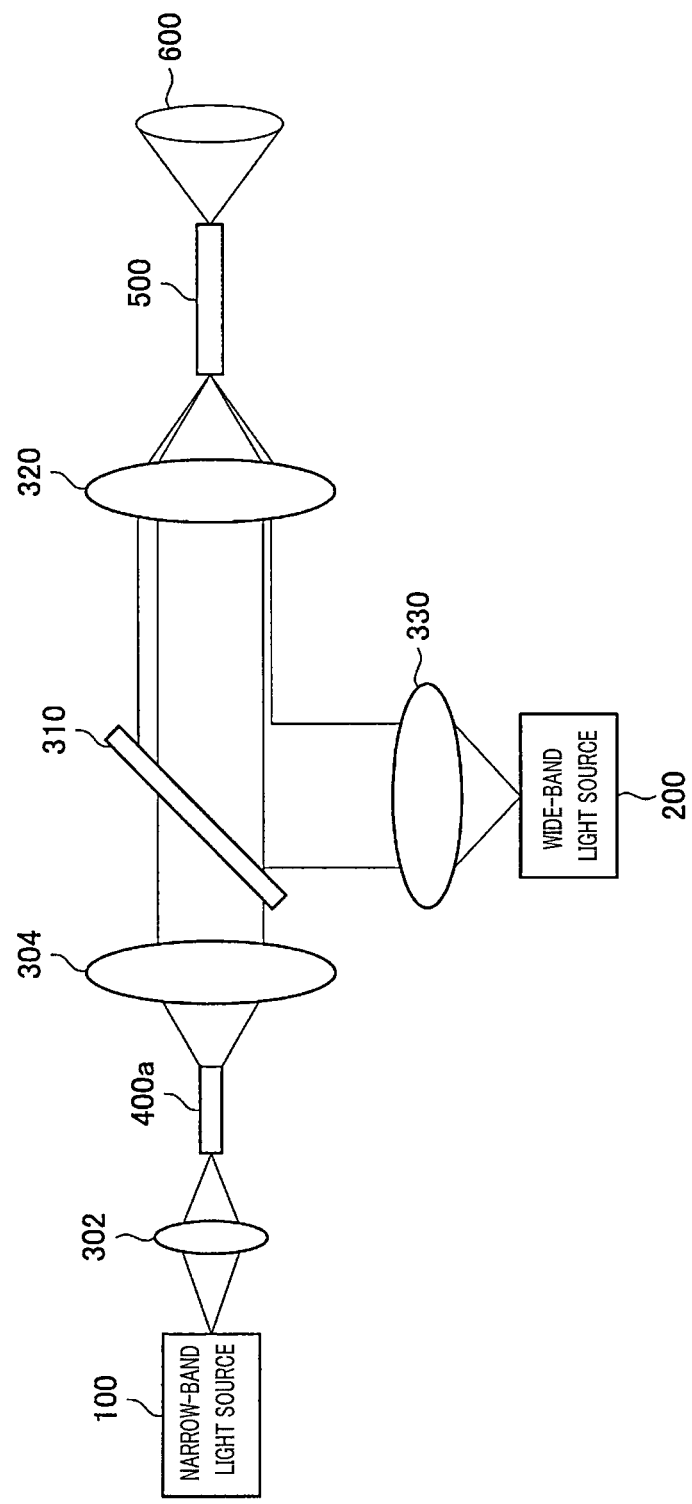
FIG. 8 is a schematic diagram showing an example in which a rod integrator is used as an emission angle converting element.

Alternatively a rod integrator can also be used as the emission angle converting element 400. FIG. 8 is a schematic diagram showing an example in which a rod integrator 400*a* is used as the emission angle converting element 400. While the lens 300 that collimates the narrow-band light is provided in FIG. 1, a lens 302 that collects the narrow-band light on the rod integrator 400*a* is provided in FIG. 8. Using the rod integrator 400*a* as the emission angle converting element 400 enables transmission efficiency of light to be increased.

The rod integrator 400*a* is constituted by, for example, a transparent glass material and has a prismatic shape instead of a columnar shape. The narrow-band light incident to the rod integrator 400*a* is repeatedly totally reflected inside the rod integrator 400*a* and is emitted from an end surface on an opposite side to an incidence-side end surface. Accordingly an NFP (Near Field Pattern) is created which is uniform across an entire end surface from where the narrow-band light is emitted, and when changed to an FFP (Far Field Pattern), the emission angle distribution of the narrow-band light is converted and an emission angle of the narrow-band light can be widened as shown in FIG. 5. The light emitted from the rod integrator 400*a* is collimated by the lens 304, passes through the combining dichroic mirror 310, and is collected on the light guide 500 by the lens 320.

6. EXAMPLE OF NA LIMITATION OF WIDE-BAND LIGHT

Figure 9:
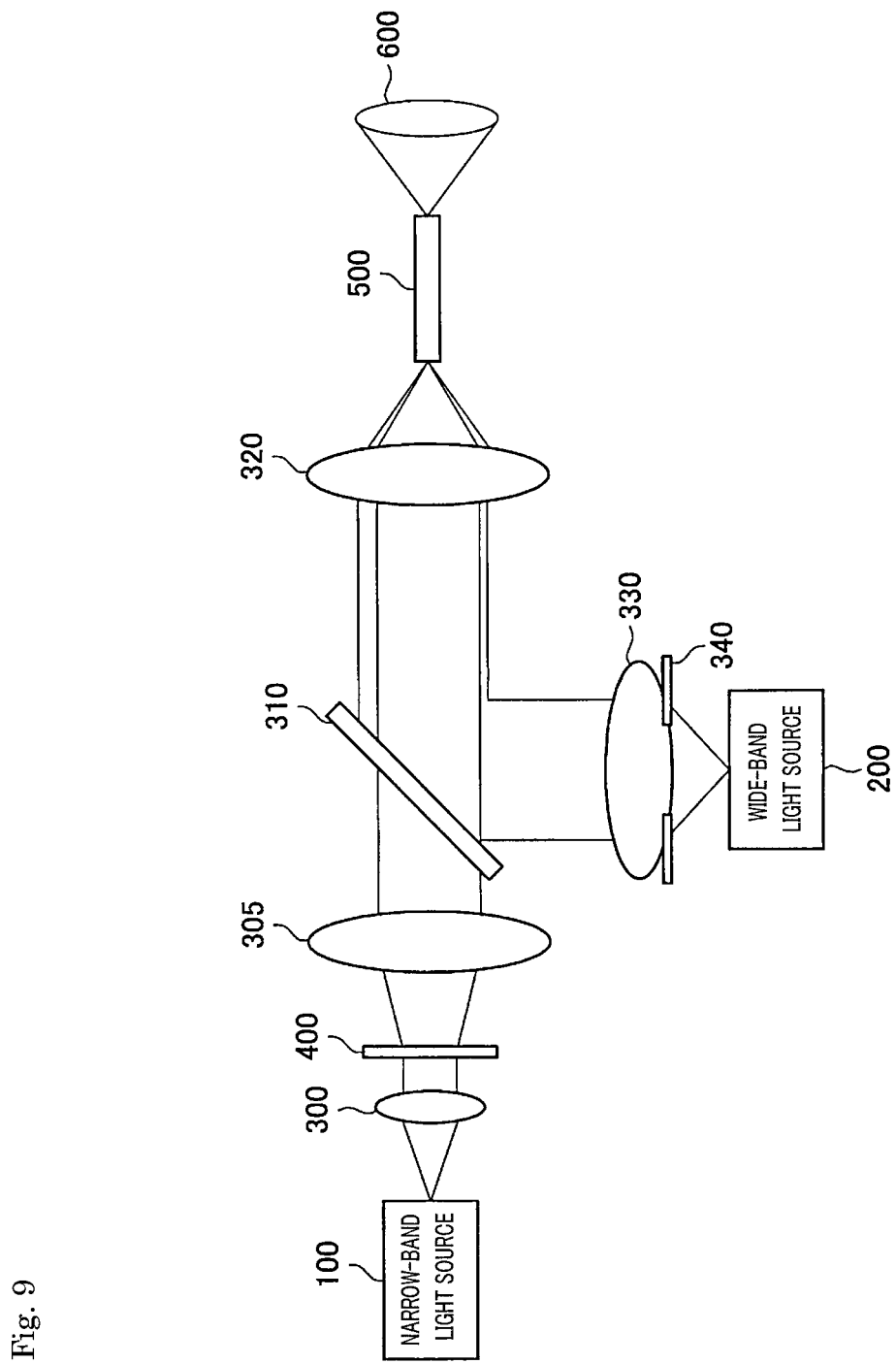
FIG. 9 is a schematic diagram showing a method of limiting an NA of wide-band light using an aperture.
Figure 10:
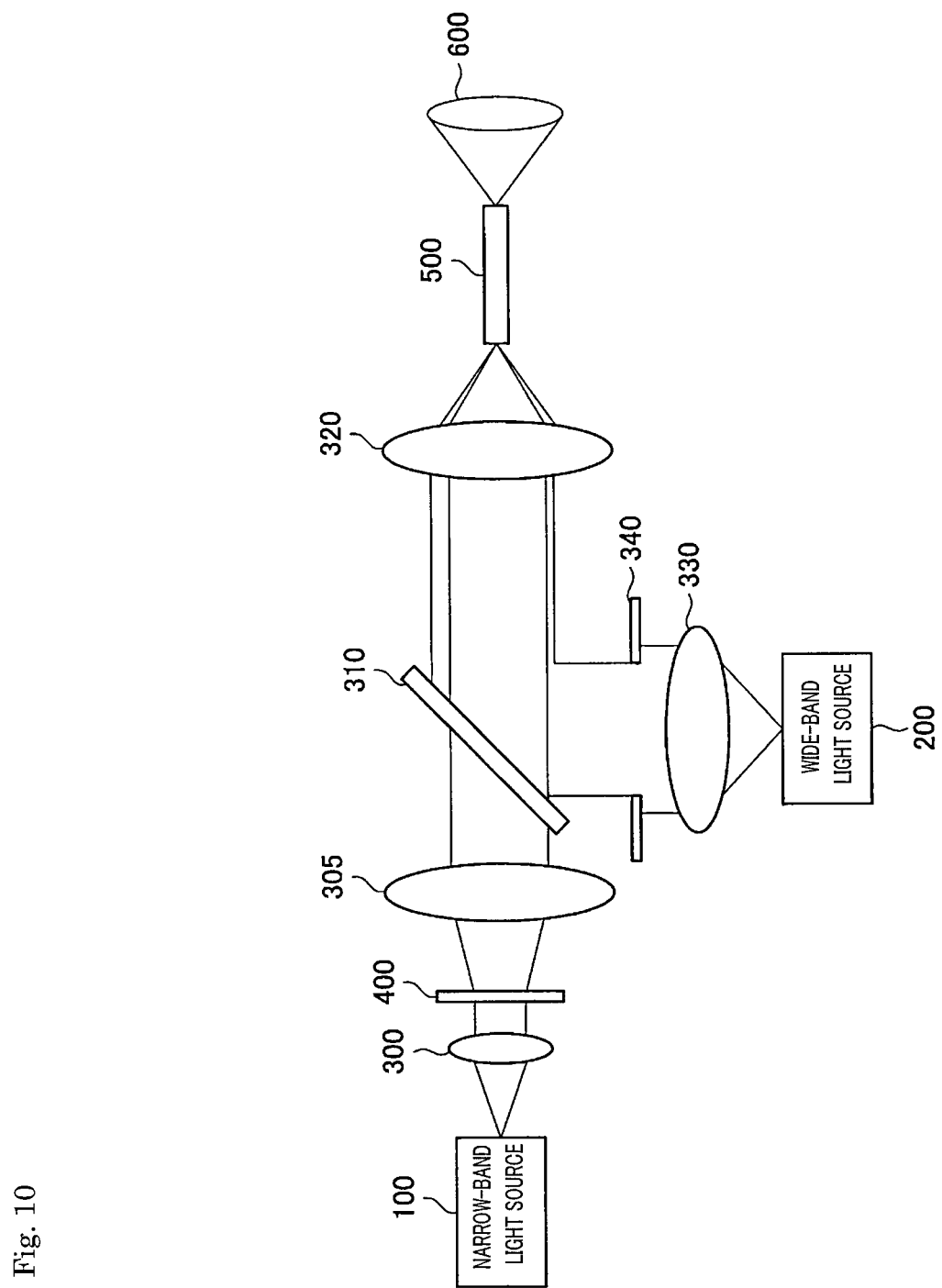
FIG. 10 is a schematic diagram showing a method of limiting an NA of wide-band light using an aperture.

As described above, limitation of an NA of the wide-band light can be performed by the lens 330. On the other hand, NA limitation of the wide-band light can also be performed by providing apertures before and after the lens 330. FIGS. 9 and 10 are schematic diagrams showing a method of limiting an NA of the wide-band light using an aperture. In an example shown in FIG. 9, an aperture 340 is provided on a front side (a side of the wide-band light source 200) of the lens 330. In addition, in an example shown in FIG. 10, an aperture 340 is provided on a rear side (a side of the dichroic mirror 310) of the lens 330. In this manner, NA limitation of the wide-band light can also be performed by providing apertures. Accordingly the characteristics of the wide-band light shown in FIG. 6 can be obtained in a similar manner to a case where an NA limitation is applied using the lens 330.

7. CONFIGURATION EXAMPLE OF NARROW-BAND LIGHT SOURCE

Figure 11:
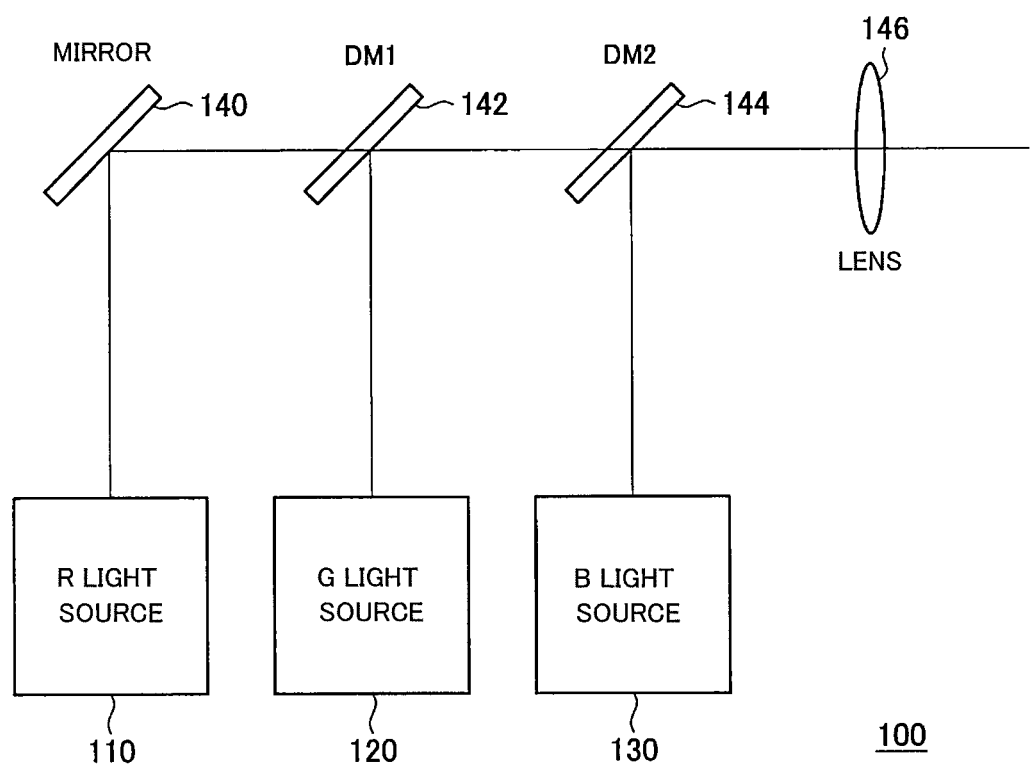
FIG. 11 is a schematic diagram showing an example of a narrow-band light source that creates narrow-band light by combining a plurality of wavelengths.

Narrow-band light is not limited to light with a single wavelength and may be light combining a plurality of wavelengths. FIG. 11 is a schematic diagram showing an example of the narrow-band light source 100 that creates narrow-band light by combining a plurality of wavelengths. As shown in FIG. 11, the narrow-band light source 100 is constituted by a red light source 110, a green light source 120, a blue light source 130, a mirror 140, a dichroic mirror (DM1) 142, a dichroic mirror (DM2) 144, and a condenser lens 146.

Each of the red light source 110, the green light source 120, and the blue light source 130 is constituted by a semiconductor laser and is independently driven. For example, a GaInP quantum well structure laser diode (RLD) is used as the red light source 110, a GaInN quantum well structure laser diode (GLD) is used as the green light source 120, and a GaInN quantum well structure laser diode (BLD) is used as the blue light source 130.

Red light emitted from the red light source 110 is reflected at an angle of 45 degrees by the mirror 140, passes through the dichroic mirror 142 and the dichroic mirror 144, and is collected by the condenser lens 146. Green light emitted from the green light source 120 is emitted toward the dichroic mirror 142, and blue light emitted from the blue light source 130 is emitted toward the dichroic mirror 144.

The dichroic mirror 142 has optical characteristics of transmitting a red wavelength and reflecting a green wavelength. The dichroic mirror 144 has optical characteristics of transmitting a red wavelength and a green wavelength and reflecting a blue wavelength. The red wavelength from the red light source 110 is combined with the green wavelength from the green light source 120 by the dichroic mirror 142 and then combined with the blue wavelength from the blue light source 130 by the dichroic mirror 144. The combined light is collected by the condenser lens 146. By combining a red wavelength, a green wavelength, and a blue wavelength as described above, a laser of white light can be emitted from the narrow-band light source 100.

8. CONFIGURATION EXAMPLE OF NARROW-BAND LIGHT SOURCE INCLUDING YELLOW LIGHT SOURCE

Figure 12:
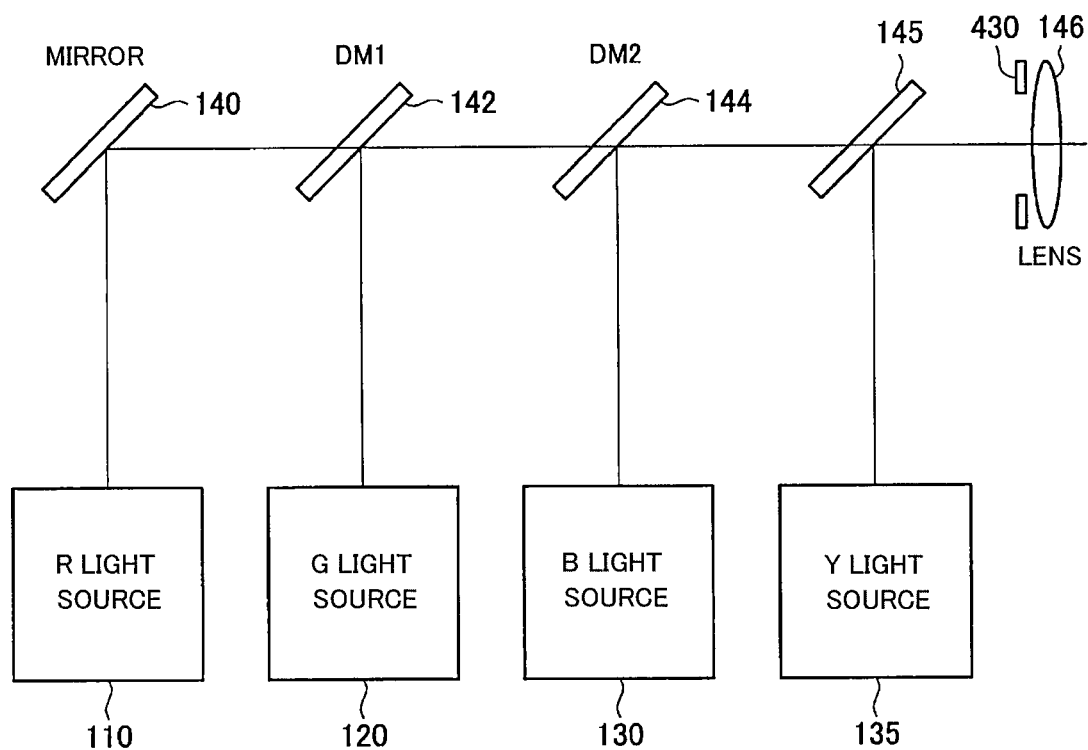
FIG. 12 is a schematic diagram showing a configuration example in which a yellow light source, a dichroic mirror, and an aperture are added to the narrow-band light source shown in FIG. 11.

FIG. 12 is a schematic diagram showing a configuration example in which a yellow light source 135, a dichroic mirror 145, and an aperture 430 are added to the narrow-band light source 100 shown in FIG. 11. The yellow light source 135 is constituted by a semiconductor laser. The red wavelength from the red light source 110 is combined with the green wavelength from the green light source 120 by the dichroic mirror 142, next combined with the blue wavelength from the blue light source 130 by the dichroic mirror 144, and then combined with a yellow wavelength from the yellow light source 135 by the dichroic mirror 145.

Therefore, according to the configuration example shown in FIG. 12, by combining a red wavelength, a green wavelength, a blue wavelength, and a yellow wavelength, white light with a more optimally adjusted hue than the narrow-band light source 100 shown in FIG. 11 can be obtained. As a result, the light source apparatus 1000 can be solely constituted by the narrow-band light source 100 without specifically having to provide the wide-band light source 200 such as that shown in FIG. 1.

In addition, according to the configuration example shown in FIG. 12, emission angles of the red laser light, the green laser light, the blue laser light, and the yellow laser light respectively emitted from the red light source 110, the green light source 120, the blue light source 130, and the yellow light source 135 all have a Gaussian distribution. Therefore, according to the configuration example shown in FIG. 12, unlike when combining the narrow-band light with the wide-band light, since distributions of emission angles of the respective colors are the same, unevenness does not occur in white light after combination.

On the other hand, according to the configuration example shown in FIG. 12, since the emission angles of the red laser light, the green laser light, the blue laser light, and the yellow laser light have a Gaussian distribution, light intensity in a periphery declines as compared to a center. In consideration thereof, by providing the aperture 430 such as that shown in FIG. 12 and removing peripheral light, white light with more uniform intensity within an irradiation range can be generated. Therefore, according to the configuration shown in FIG. 12, white light with suppressed unevenness and uniform intensity can be emitted.

In addition, in the configuration example shown in FIG. 12, heat can be generated at the aperture 430 by subjecting the aperture 430 to NA limitation. Accordingly heat generation by the light guide 500 and the like outside of the light source apparatus 1000 can be suppressed.

Figure 13:
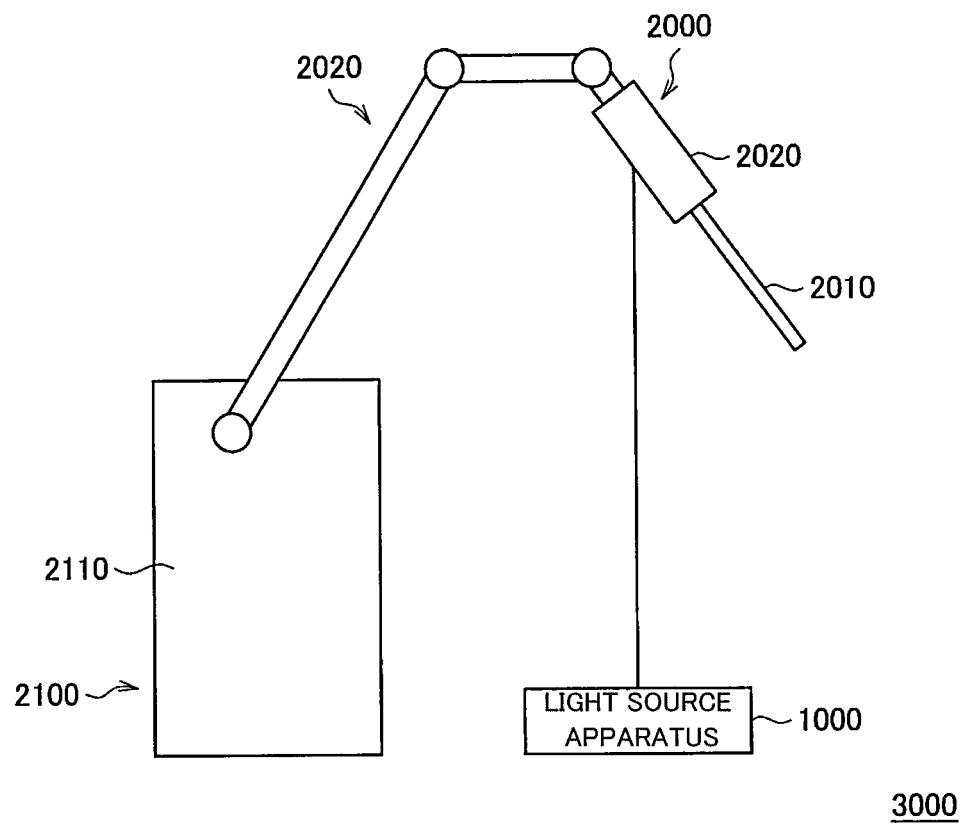
FIG. 13 is a diagram showing an example of a schematic configuration of an endoscopic surgery system to which the light source apparatus according to the present disclosure can be applied.

9. CONFIGURATION EXAMPLE OF MEDICAL SYSTEM 9.1. Configuration Example of Endoscopic System FIG. 13 is a diagram showing an example of a schematic configuration of an endoscopic surgery system 3000 to which the light source apparatus 1000 according to the present disclosure can be applied. The endoscopic surgery system 3000 is constituted by an endoscope 2000, a support arm apparatus 2100 for supporting the endoscope 2000, and the light source apparatus 1000.

The support arm apparatus 2100 includes an arm portion 2020 that stretches from a base portion 2110. In the illustrated example, the arm portion 2020 is constituted by a plurality of joint portions and a plurality of links and is driven under control of an arm control apparatus. The arm portion 2020 supports the endoscope 2000 and controls a position and an attitude thereof. Accordingly stable fixation of the position of the endoscope 2000 can be realized.

The endoscope 2000 is constituted by a lens tube 2010 of which a region of a predetermined length from a tip is to be inserted into the body cavity of a patient and a camera head 2020 that is connected to a base end of the lens tube 2010. The endoscope 2000 may be configured as a so-called rigid scope having a rigid lens tube 2010 or may be configured as a so-called flexible scope having a flexible lens tube 2010.

An opening fitted with an objective lens (the observation optical system 600) is provided at the tip of the lens tube 2010. The light source apparatus 1000 is connected to the endoscope 2000, and light generated by the light source apparatus 1000 is guided to the tip of the lens tube 2010 by the light guide 500 that is provided so as to extend inside the lens tube 2010 and irradiated via the objective lens toward an observation target inside the body cavity of the patient.

An optical system and an imaging element are provided inside the camera head 2020, and reflected light (observation light) from the observation target is collected on the imaging element by the optical system. The observation light is photoelectrically converted by the imaging element and an electric signal corresponding to the observation light or, in other words, an image signal corresponding to an observation image is generated. The image signal is transmitted to a CCU (Camera Control Unit) as RAW data. The camera head 2020 is mounted with a function for adjusting a magnification and a focal length by suitably driving an optical system thereof.

For example, the camera head 2020 may be provided with a plurality of imaging elements in order to accommodate stereoscopic viewing (3D display) or the like. In this case, relay optical systems are provided in plurality inside the lens tube 2010 in order to guide observation light to each of the plurality of imaging elements.

9.2. Configuration Example of Microscopic System

Figure 14:
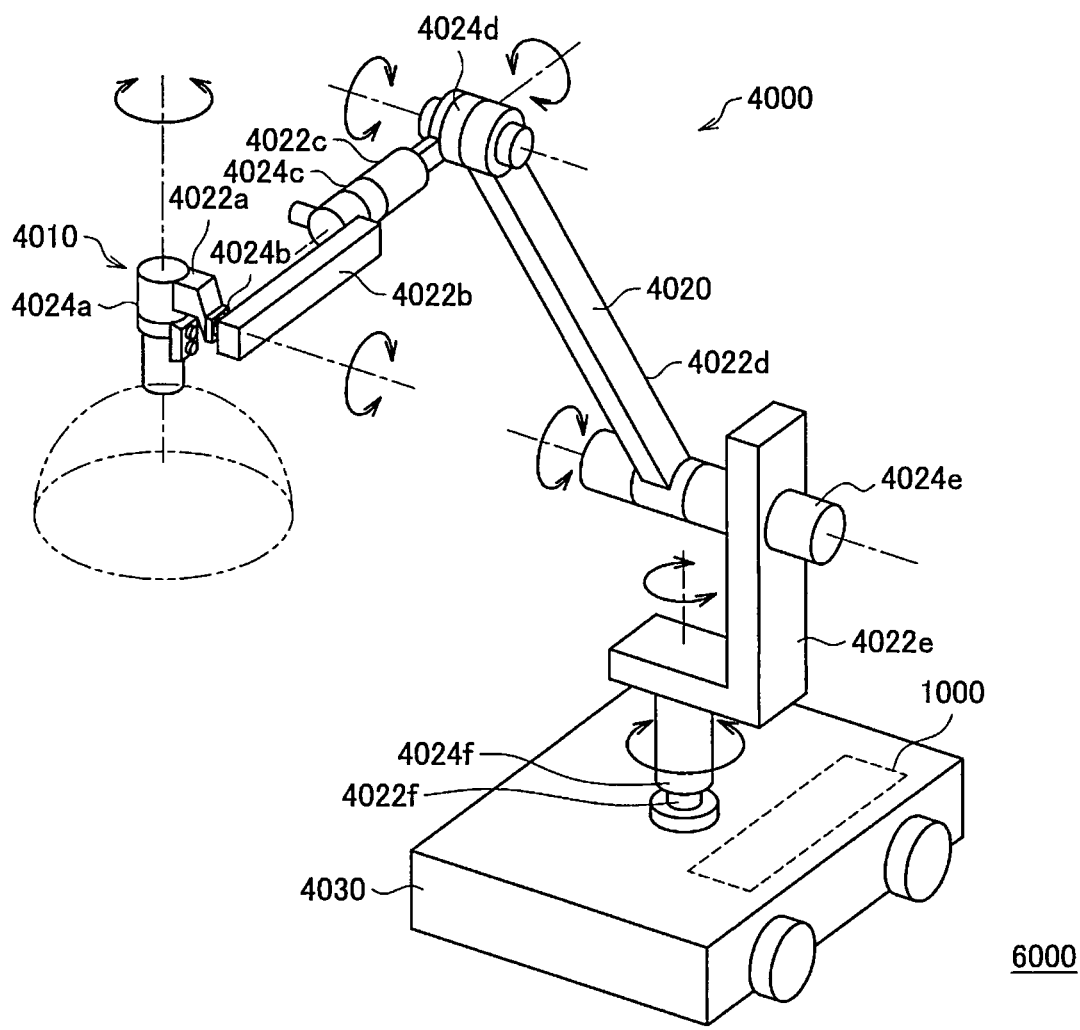
FIG. 14 is a diagram showing an example of a schematic configuration of a microscopic surgery system to which the light source apparatus according to the present disclosure can be applied.

FIG. 14 is a diagram showing an example of a schematic configuration of a microscopic surgery system 6000 to which the light source apparatus 1000 according to the present disclosure can be applied. Referring to FIG. 14, the microscopic surgery system 6000 is constituted by a microscope apparatus 4000 and the light source apparatus 1000.

The microscope apparatus 4000 has a microscope portion 4010 for enlarging and observing an observation object (an operative site of a patient), an arm portion 4020 that supports the microscope portion 4010 at a tip thereof, and a base portion 4030 that supports a base end of the arm portion 4020.

The microscope portion 4010 is an electronic imaging-type microscope portion (a so-called video-type microscope portion) which electronically creates a captured image using an imaging unit. Light (hereinafter, also referred to as observation light) from an observation object enters the imaging unit inside the microscope portion 4010.

The imaging unit is constituted by an optical system that collects observation light and an imaging element that receives observation light collected by the optical system. The optical system is constructed by combining a plurality of lenses including a zoom lens and a focus lens and optical characteristics thereof are adjusted so that the observation light is focused on a light-receiving surface of the imaging element. The imaging element receives and photoelectrically converts the observation light to generate a signal corresponding to the observation light or, in other words, an image signal corresponding to an observation image. As the imaging element, for example, an imaging element which has a Bayer array and which is capable of color photography is used. The imaging element may be various known imaging elements such as a CMOS (Complementary Metal Oxide Semiconductor) image sensor or a CCD (Charge Coupled Device) image sensor.

The arm portion 4020 is constructed by coupling a plurality of links (a first link 4022a to a sixth link 40220 by a plurality of joint portions (a first joint portion 4024a to a sixth joint portion 40240 so as to be mutually rotatable. Each joint portion is configured to be rotatable around a rotation axis indicated by a dashed-dotted line.

The number and a shape (a length) of the links, the number, arrangement positions, and directions of rotation axes of the joint portions, and the like constituting the illustrated arm portion 4020 may be appropriately designed so as to realize a desired degree of freedom. In addition, the first joint portion 4024a to the sixth joint portion 4024f may be provided with a drive mechanism such as a motor and an actuator being mounted with an encoder or the like for detecting an angle of rotation at each joint portion. Furthermore, by appropriately controlling drive of each actuator provided at the first joint portion 4024a to the sixth joint portion 4024f, an attitude of the arm portion 4020 or, in other words, a position and an attitude of the microscope portion 4000 can be controlled.

For example, the light source apparatus 1000 is built into the base portion 4030. The light guide 500 connected to the light source apparatus 1000 is passed inside or outside of the first link 4022a to the sixth link 4022f and guided to the microscope portion 4010. By irradiating an observation object with light from the tip of the light guide 500 having been guided to the microscope portion 4010, when the imaging unit inside the microscope portion 4010 images an observation object (an affected area) of a patient, brightness of the observation object can be increased and the observation object can be clearly imaged.

As described above, according to the present embodiment, by causing narrow-band light to enter the emission angle converting element 400, emission angle distributions of the narrow-band light and the wide-band light can be brought close to each other and unevenness of irradiating light can be reduced. In addition, combining the wide-band light with the narrow-band light improves color rendering properties. Accordingly when generating the narrow-band light with a semiconductor laser, illuminating light which has high color rendering properties and in which an occurrence of unevenness has been suppressed can be collected on a small-diameter light guide in an efficient manner. Furthermore, converting an emission angle of the narrow-band light so as to match the emission angle distribution of the wide-band light enables a decline in light intensity in a periphery to be suppressed.

While a preferred embodiment of the present disclosure has been described in detail with reference to the accompanying drawings, the technical scope of the present disclosure is not limited thereto. It will be obvious to a person with ordinary skill in the art to which the technical field of the present disclosure pertains that various modifications and changes can be arrived at without departing from the scope of the technical ideas as set forth in the appended claims and, as such, it is to be understood that such modifications and changes are to be naturally covered in the technical scope of the present disclosure.

For example, while an example of a light source apparatus for medical use has been explained in the embodiment described above, the present technique is not limited to the example. The present embodiment can be widely applied to general light source apparatuses including industrial light source apparatuses.

Furthermore, the advantageous effects described in the present specification are merely descriptive or exemplary and not restrictive. In other words, the technique according to the present disclosure can produce, in addition to or in place of the advantageous effects described above, other advantageous effects that will obviously occur to those skilled in the art from the description of the present specification.

The following configurations are also covered in the technical scope of the present disclosure.

(1)

A medical system, including:
 a medical device provided with an imaging unit configured to image an observation object; and
 a light source apparatus configured to generate light to irradiate the observation object, wherein
 the light source apparatus has:
 a narrow-band light source configured to emit narrow-band light of which a wavelength width is a narrow band;
 a wide-band light source configured to emit wide-band light of which the wavelength width is wider than the narrow-band light;
 a combining unit configured to combine the narrow-band light and the wide-band light; and
 an emission angle converting unit configured to convert an emission angle of the narrow-band light.

(2)

A medical light source apparatus, including:
 a narrow-band light source configured to emit narrow-band light of which a wavelength width is a narrow band;
 a wide-band light source configured to emit wide-band light of which the wavelength width is wider than the narrow-band light;
 a combining unit configured to combine the narrow-band light and the wide-band light; and
 an emission angle converting unit configured to convert an emission angle of the narrow-band light.

(3)

The medical light source apparatus according to (2), wherein the emission angle converting unit is configured to widen an emission angle distribution of the narrow-band light.

(4)

The medical light source apparatus according to (3), wherein the emission angle converting unit is configured to widen an emission angle distribution of the narrow-band light and bring the emission angle distribution of the narrow-band light closer to an emission angle distribution of the wide-band light.

(5)

The medical light source apparatus according to any one of (2) to (4), including a lens configured to collimate the narrow-band light incident to the emission angle converting unit.

(6)

The medical light source apparatus according to any one of (2) to (5), wherein the emission angle converting unit is constituted by a diffuser plate configured to diffuse the narrow-band light.

(7)

The medical light source apparatus according to any one of (2) to (5), wherein the emission angle converting unit is constituted by a fly-eye lens.

(8)

The medical light source apparatus according to any one of (2) to (5), wherein the emission angle converting unit is constituted by a rod integrator.

(9)

The medical light source apparatus according to any one of (2) to (8), further including an emission angle limiting unit configured to limit an emission angle of the wide-band light.

(10)

The medical light source apparatus according to (9), wherein the emission angle limiting unit is constituted by a lens configured to transmit the wide-band light.

(11)

The medical light source apparatus according to (9), wherein the emission angle limiting unit is constituted by an aperture configured to transmit the wide-band light.

(12)

The medical light source apparatus according to any one of (2) to (11), wherein the narrow-band light source is constituted by a laser light source.

(13)

The medical light source apparatus according to (12), wherein the narrow-band light source is constituted by a red laser light source configured to generate red light,
a green laser light source configured to generate green light, and
a blue laser light source configured to generate blue light, and the narrow-band light source is configured to emit white light by combining the red light, the green light, and the blue light.

(14)

The medical light source apparatus according to any one of (2) to (13), including a light guide configured to be irradiated by the narrow-band light and the wide-band light having been combined by the combining unit.

(15)

The medical light source apparatus according to any one of (2) to (14), wherein an observation object of a patient is to be irradiated by the narrow-band light and the wide-band light having been combined by the combining unit.

(16)

A method in a medical light source apparatus including the steps of combining narrow-band light of which a wavelength width is a narrow band and wide-band light of which the wavelength width is wider than the narrow-band light; and
converting an emission angle of the narrow-band light prior to combining the narrow-band light and the wide-band light.

REFERENCE SIGNS LIST

100 Narrow-band light source
110 Red light source
120 Green light source
130 Blue light source
200 Wide-band light source
310 Dichroic mirror
330 Lens
340, 350 Aperture
400 Emission angle converting element
1000 Light source apparatus
2000 Endoscope
3000 Endoscopic surgery system
4000 Microscope apparatus
6000 Microscopic surgery system

The invention claimed is:

1. A medical system, comprising:
a medical device provided with an imaging unit configured to image an observation object; and
a light source apparatus configured to generate light to irradiate the observation object, wherein
the light source apparatus includes:
a narrow-band light source configured to emit narrow-band light of which a wavelength width is a narrow band;
a wide-band light source configured to emit wide-band light of which the wavelength width is wider than the narrow-band light;
a first optical element to combine the narrow-band light and the wide-band light;
an aperture configured to block a portion of the wide-band light between the wide-band light source and the first optical element to reduce an intensity of the wide-band light; and
a top-hat diffuser plate in an optical path of the narrow-band light source to widen an emission angle distribution of the narrow-band light incident on the first optical element to match an emission angle profile of the wide-band light incident on the first optical element.

2. The medical system according to claim 1, wherein the top-hat diffuser plate is between the narrow-band light source and the first optical element.

3. The medical system according to claim 1, further comprising a third optical element is a lens configured to transmit the wide-band light.

4. The medical system according to claim 1, further comprising a second optical element to collimate the narrow-band light incident on the top-hat diffuser plate.

5. A medical light source apparatus, comprising:
a narrow-band light source configured to emit narrow-band light of which a wavelength width is a narrow band;
a wide-band light source configured to emit wide-band light of which the wavelength width is wider than the narrow-band light;
a first optical element to combine the narrow-band light and the wide-band light;
an aperture configured to block a portion of the wide-band light between the wide-band light source and the first optical element to reduce an intensity of the wide-band light; and
a top-hat diffuser plate in an optical path of the narrow-band light source to widen an emission angle distribution of the narrow-band light incident on the first optical element to match an emission angle profile of the wide-band light incident on the first optical element.

6. The medical light source apparatus according to claim 5, comprising a second optical element to collimate the narrow-band light incident on the top-hat diffuser plate.

7. The medical light source apparatus according to claim 5, further comprising a lens configured to transmit the wide-band light.

8. The medical light source apparatus according to claim 5, wherein the narrow-band light source is a laser.

9. The medical light source apparatus according to claim 8, wherein
the narrow-band light source includes
a red laser to generate red light,
a green laser to generate green light, and
a blue laser to generate blue light, and
the narrow-band light source is configured to emit white light by combining the red light, the green light, and the blue light.

10. The medical light source apparatus according to claim 5, comprising a light guide configured to be irradiated by the narrow-band light and the wide-band light having been combined by the first optical element.

11. The medical light source apparatus according to claim 5, wherein an observation object of a patient is to be irradiated by the narrow-band light and the wide-band light having been combined by the first optical element.

12. The medical light source apparatus according to claim 5, wherein the top-hat diffuser plate is between the narrow-band light source and the first optical element.

13. The medical light source apparatus according to claim 8, wherein
the narrow-band light source further includes a yellow laser to generate yellow light and the narrow-band light source is configured to emit white light by combining the red light, the green light, the blue light, and the yellow light.

14. A method in a medical light source apparatus comprising:
combining narrow-band light of which a wavelength width is a narrow band and wide-band light of which the wavelength width is wider than the narrow-band light; and
matching an emission angle profile of the narrow-band light of the narrow-band light to an emission angle profile of the wide-band light by transmitting the narrow-band light through a top-hat diffuser plate to widen the emission angle Profile of the narrow-band light prior to combining the narrow-band light and the wide-band light and blocking a portion of the wide-band light using an aperture to reduce an intensity of the wide-band light prior to combining the narrow-band light and the wide-band light.

15. The method according to claim 14, further comprising irradiating a light guide with combined narrow-band light and wide-band light.

16. The method according to claim 14, further comprising irradiating an observation object of a patient with combined narrow-band light and wide-band light.

* * * * *